United States Patent [19]

McCague et al.

[11] Patent Number: 5,739,332
[45] Date of Patent: Apr. 14, 1998

[54] CYCLOALKANEDIOLS AND THEIR USE IN PREPARING CHIRAL COMPOUNDS

[75] Inventors: Raymond McCague, Cambridgeshire; Graham Ruecroft; Christopher Palmer, both of Cambridge, all of United Kingdom

[73] Assignee: Chiroscience Limited, Cambridge, United Kingdom

[21] Appl. No.: 615,180

[22] PCT Filed: Oct. 7, 1994

[86] PCT No.: PCT/GB94/02194

§ 371 Date: Jun. 4, 1996

§ 102(e) Date: Jun. 4, 1996

[87] PCT Pub. No.: WO95/09839

PCT Pub. Date: Apr. 13, 1995

[30] Foreign Application Priority Data

Oct. 7, 1993 [GB] United Kingdom ............ 9320643

[51] Int. Cl.⁶ ............ C07C 271/24; C07D 317/44
[52] U.S. Cl. ............ 544/277; 544/329; 549/436; 560/115; 560/189; 560/158
[58] Field of Search ............ 560/115, 189, 560/158; 549/436; 544/277, 329

[56] References Cited

U.S. PATENT DOCUMENTS 5,217,982  6/1993  Fink et al. ............ 514/352

FOREIGN PATENT DOCUMENTS 0 368 640  5/1990  European Pat. Off. .

OTHER PUBLICATIONS

Jen Chen et al., "A Novel and Efficient Route to Chiral 2-Substituted Carbocyclic 5'-N-Ethyl-Carboxamido-Adenosine (C-NECA)", Tetrahedron Letters, vol. 30, No. 41, 1989, pp. 5543-5546.

Primary Examiner—Richard L. Raymond
Attorney, Agent, or Firm—Foley & Lardner

[57] ABSTRACT

A process for the product of a 2,3-cis-dihydroxycycloalkane-1-carboxamide, comprises dihydroxylation of the corresponding cycloalkene-1-carboxamide. Some products are new. The stereoselective dihydroxylation is surprising.

14 Claims, No Drawings

CYCLOALKANEDIOLS AND THEIR USE IN PREPARING CHIRAL COMPOUNDS

This application is a 371 of PCT/GB94/02194, filed Oct. 7, 1994.

FIELD OF THE INVENTION

This invention relates to cycloalkanediols and their use in preparing chiral compounds. The invention relates also to a process whereby a desired diol can be prepared stereoselectively.

BACKGROUND OF THE INVENTION 2,3-cis-Dihydoxycyclopentane-1-carboxamides linked at the 5-position to a purine or pyrimidine have therapeutic utility. See, for example, EP-A-0368640. In the synthesis of such compounds, control of the chiral centres on the cyclopentane ring is essential.

An important intermediate in such a synthesis, which is protected at the hydroxyl groups as an acetonide, is the final compound in Scheme 1, below; this compound is useful as a synthon for the manufacture of carbocylic compounds having vasodilatory activity, see Chen et al, Tetrahedron Lett, 30:5543-6 (1989). An established route for the synthesis of the acetonide is also shown in Scheme 1.

The geometric constraints provided by the bicyclic nature of the starting material, 2-azabicyclo[2.2.1]hept-5-en-3-one, are thought to be the reason for the high stereocontrol of the dihydroxylation onto the exo-face of the starting material. One disadvantage, however, with this route is the need for a pressure reaction to open the amide linkage.

However, despite these disadvantages, it is generally considered that opening of the amide linkage of the starting material results in a loss of the stereocontrol of the dihydroxylation so that a mixture of stereoisomers of the diol results. This is undesirable.

SUMMARY OF THE INVENTION

According to the present invention, a process for the preparation of a 2,3-dihydroxycycloalkene-1-carboxamide, e.g. of formula (1) and most preferably the diol corresponding to the acetonide shown in Scheme 1, comprises stereoselective dihydroxylation of the olefinic precursor thereof. Dihydroxylation takes place anti to the carboxamide function.

The process can be used to prepare a substantially pure diastereomer, either as a single enantiomer, or in racemic form. Indeed the optical purity of the product will reflect the optical composition of the starting cyclopentene.

In view of the understanding in the art as to the importance of a bicyclic structure for achieving high stereocontrol of a reaction of this nature, it is surprising that the process of the invention, i.e. without a bicyclic starting material, achieves just this.

DESCRIPTION OF THE INVENTION

Compounds of the type involved in the novel process are shown in Scheme 2. n may be any suitable number, e.g. 1 or 2, and $(CH_2)_n$ may be substituted, e.g. by a primary, secondary, tertiary or cyclic amine function. That may be a purine or pyrimidine ring or a group $NR_3R_4$ as shown in formula (1). $R_3$ and $R_4$ are each H or a removable blocking group such as tert-butoxycarboxyl or benzyloxycarboxyl.

The starting materials for the process of the invention can be obtained by conventional methods such as amidation of the corresponding carboxylic acid or by treatment of an N-acyl-2-azabicyclo[2.2.1]hept-5-en-3-one with an amine.

Compounds of formula (1) are specific examples of products of Scheme 2, i.e. of formula (2). The nature of $R_1$ and $R_2$ is not critical; $R_1$ is preferably H, but may be any organic, e.g. hydrocarbyl group, e.g. of up to 20 C atoms. $R_2$ may be the same or a different organic group, e.g. alkyl such as ethyl. It is most preferred that $R_1$ is H, methyl or ethyl and $R_2$ is methyl or ethyl.

An example of the process of the invention is shown in Scheme 3. Starting material is depicted as a salt, but can be in the form of an amino-acid. Introduction of the ethylamido group into the starting material is relatively easy compared with its introduction in Scheme 1 which, as mentioned above, requires a pressure reaction. It may be achieved using (i) $(tBuO_2C)_2O$ and OH, and (ii) EtOCOCl and $EtNH_2$. Conversion of the cyclopentene-carboxamide, the olefinic precursor of the diol, is by cis-dihydroxylation across the double bond, for example by using osmium tetroxide or (potassium) permanganate. In the case of osmium tetroxide, that may be used as a catalyst, with stoichiometric N-methyl morpholine-N-oxide and aqueous acetone.

Further investigation into the surprising stereo selectivity observed in Scheme 3 has indicated that the origin of that stereoselectivity lies with the presence of the carboxamide functionality. When Scheme 3 is carried out with the corresponding olefinic precursor in which the carboxamide is replaced by a methyl ester function, a mixture of stereoisomers, in a ratio of about 1:1 is observed. For the given reaction, a substantially single diastereomer of the required configuration (endo or exo) is attained.

The trans-cyclopentene gave predominantly (rather than exclusively) the dihydroxylation anti to the carboxamide. This shows that the carboxamide controls the stereoselectivity, although the degree of exclusivity depends on the configuration at the other chiral centre. See Example 4, below.

It is to be noted that the process of the invention works regardless of the enantiomeric composition of the starting material, i.e. whether racemic, enantiomerically-enriched or enantiopure.

Compounds of formula (1) and the products of Scheme 2, if used as synthons, are preferably protected as the acetonide. This may be achieved by the addition of any suitably protected alkanediol, e.g. 2,2-dimethoxypropane. The synthon may then be used, by appropriate reaction with the $NR_3R_4$ group, to introduce a purine or pyrimidine ring, and also removal or substitution of the carboxamide group, e.g. to give a hydrogen atom or alkyl group at that position. All these reactions may be conducted under conditions known to those skilled in the art.

The following Examples illustrate the invention. The following Table gives the products of the Examples, with reference to formula (3).

|      | $R^1$    | $R^2$    | $R^3$                  | $R^4$           |
|------|----------|----------|------------------------|-----------------|
| (3a) | —CONHEt  | —H       | —NHCO$_2^t$Bu          | —H              |
| (3b) | —CONMe$_2$ | —H     | —NHCO$_2^t$Bu          | —H              |
| (3c) | —CONHMe  | —H       | —NHCO$_2^t$Bu          | —H              |
| (3d) | —CONHEt  | —H       | —NHCOPh                | —H              |
| (3e) | —H       | —NHCOPh  | —CONHEt                | —H              |
| (3f) | —H       | —CONHEt  | —NHCOPh                | —H              |
| (3g) | —CO$_2$Me | —H      | —NHCO$_2^t$Bu          | —H              |
| (3h) | —H       | —CO$_2$Me | —H                    | —NHCO$_2^t$Bu   |

-continued

| | $R^1$ | $R^2$ | $R^3$ | $R^4$ |
|---|---|---|---|---|
| (3i) | —$CO_2Me$ | —H | —H | —$NHCO_2^tBu$ |
| (3j) | —H | —$CO_2Me$ | —$NHCO_2^tBu$ | —H |
| (3k) | —$CO_2Me$ | —H | —H | —NHCOPh |
| (3l) | —H | —$CO_2Me$ | —NHCOPh | —H |

EXAMPLE 1

[1(R),5(S),6(S),8(S)]-6-(t-Butoxycarbonylamino)-N-ethyl-3,3-dimethyldioxabicyclo-[3.3.0]octan-8-carboxamide (3a).

A solution of [1(S),4(R)]-4-(t-butoxycarbonylamino)-N-ethyl-2-cyclopentenecarboxamide (4.82 g, 18.8 mmol), osmium tetroxide (1.5 ml of 0.5% wt aq. soln,) and N-methylmorpholine-N-oxide (2.28 g, 19.5 mmol) in 4:1 acetone/water (100 ml) was heated at reflux for 8 h. Florisil (15 g) and 10% sodium bisulphite (20 ml) were added. The solids were removed by fitration and the solution concentrated under reduced pressure. The residue was taken up in 2,2-dimethoxypropane (150 ml) containing 4-toluenesulphonic acid (20 mg) and the mixture heated at reflux for 4 hrs, cooled to room temperature and filtered through silica. The solvent was removed under reduced pressure and the residue purified by chromatography (silica; 3:1 ethyl acetate/pentane to give the title acetonide (3a; 2.24 g): NMR ($CDCl_3$): δ 6.5 (1H, d, NHBOC), 5.9 (1H, br. s, NHEt), 4.7 (1H, d, J=6 Hz, H-1), 4.5 (1H, d, J=6 Hz, H-5), 4.2 (1H, apparent t, H-6), 3.3 (2H, m, $CH_2Me$), 2.7 (1H, m, H-7), 1.4 (12H, s, $Me_3C$ and Me acetonide), 1.3 (3H, s, Me acetonide), 1.1 (3H, t, $CH_3CH_2$).

EXAMPLE 2

[1(R),5(S),6(S),8(S)]-6-(t-Butoxycarbonylamino)-N,N-dimethyl-3,3-dimethyldioxabicyclo-[3.3.0]octan-8-carboxamide (3b).

N-Methylmorpholine-N-oxide (0.438 g, 3.74 mmol) was added in one portion to a stirred solution of [1(S),4(R)]-4-(t-butoxycarbonylamino)-N,N-dimethyl-2-cyclopentenecarboxamide (0.545 g, 2.15 mmol) and osmium tetroxide (0.5 ml of 4% wt aq. soln,) in 5:1 acetone/water (12 ml) and the resulting mixture was heated at reflux for 8 h. The reaction was quenched by the addition of 10% sodium bisulphite (10 ml) and Florisil (5 g). The solids were removed by filtration and the solution concentrated under reduced pressure. The residue was taken up in 2,2-dimethoxypropane (20 ml) containing 4-toluenesulphonic acid (50 mg) and the mixture heated at reflux for 12 hrs. The resulting solution was filtered through a pad of silica and the solvent was removed under reduced pressure. The residue was purified by chromatography (silica; 1:1 to 3:1 ethyl acetate/pentane to give the title acetonide (3b; 0.32 g): NMR ($CDCl_3$): δ6.3 (1H, d, NHBOC), 4.7 and 4.5 ( each 1H, d, J=6 Hz, H-1 and H-5), 4.1 (1H, apparent t, H-6), 3.2 (4H, H-8 and MeN)), 3.0 (3H, s, MeN), 2.4 (1H, m, H-7), 1.8 (1H, m, H-7), 1.4 and 1.2 (15H, s, t-Bu and 2 x acetonide Me).

EXAMPLE 3

[1(R),5(S),6(S),8(S)]-6-(t-Butoxycarbonylamino)-N-methyl-3,3-dimethyldioxabicyclo-[3.3.0]octan-8-carboxamide (3c).

This was carried out as for Example 2 but using the alkene [1(S),4(R)]-4-(t-butoxycarbonylamino) -N-methyl-2-cyclopentenecarboxamide (0.631 g, 2.63 mmol) and N-methylmorpholine -N-oxide (0.40 g) at reflux for 2 h. The title acetonide was isolated by chromatography (silica 1:1 to 3:1 ethyl acetate/pentane) as a solid. NMR ($CDCl_3$): δ6.5 (1H, d, NHBOC), 5.9 (1H, br. s, NHEt), 4.7 (1H, d, J=6 Hz, H-1), 4.5 (1H, d, J=6 Hz, H-5), 4.2 (1H, apparent t, H-6), 3.3 (2H, m, $CH_2Me$), 2.7 (1H, m, H-7), 1.4 (12H, s, $Me_3C$ and Me acetonide), 1.3 (3H, s, Me acetonide), 1.1 (3H, t, $CH_3CH_2$).

EXAMPLE 4

Dihydroxylation of a cis-trans mixture of 4(R)-benzoylamino-N-ethylcyclopent-2-ene-1-carboxamide.

Nmethylmorpholine-N-oxide (0.60 g, 5.12 mmol) was added to a solution of the alkenes (1.5:1 cis/trans; 1.22 g, 4.73 mmol) and osmium tetroxide (1 ml of 0.5% solution in acetone/water 5:1 70 ml) and the resulting solution heated at reflux for 4 h. The reaction was allowed to cool to room temperature. 10% Sodium bisulphite (20 ml) and Florisil (20 g) were added and the solids removed by filtration. The residue was taken up in 2:1 2,2-dimethoxypropane/acetone (150 ml) containing p-toluenesulphonic acid (50 mg) and the resulting mixture heated at reflux for 5 h. The solvent was removed under reduced pressure and the residue purified by chromatography (silica 2:1 then 3:1 ethyl acetate / pentane) to give the acetonides (3d, 0.53g; 3e, 0.35g; 3f, 0.15g). NMR (3d) ($CDCl_3$): δ8.9 (1H, d, NH), 7.9 (2H, m, ArH), 7.4 (3H, m, ArH), 6.1 (1H, br. t, NH), 5.65 (3H, H-1, H-5 and H-6), 3.3 (2H, m, $CH_2Me$), 2.9 (1H, d, H-8), 2.5 (1H, m, H-7), 1.9 (1H, d, H-7), 1.4 (3H,s, Me acetonide), 1.2 (3H, s, Me acetonide), 1.1 (3H, t, J=8Hz, $CH_3CH_2$); (3e) ($CDCl_3$): δ7.8 (2H, m, ArH), 7.4 (3H, m, ArH), 6.7 (1H, br. d, NH), 5.6 (1H, br.t, NH), 4.9 (1H, d, J=7Hz, H-1), 4.7 (2H, m, H-5, H-6), 3.3 (2H, m, $CH_2Me$), 2.7 (1H, d, J=12Hz, H-8), 2.3 (1H, m, H-7), 1.9 (1H, m, H-7), 1.8 (3H,s, Me acetonide), 1.6 (3H, s, Me acetonide), 1.1 (3H, t, J=8Hz, $CH_3CH_2$); (3f) ($CDCl_3$): δ7.8 (2H, m, ArH), 7.4 (3H, m, ArH), 7.1 (1H, br. d, NH), 6.7 (1H, br.t, NH), 4.7 (2H, m, H-1 anf H-5), 4.3 (1H, apparent t, H-6), 3.1 (3H, m, $CH_3CH_2$ and H-8) 2.2 (2H, br.m, 2 x H-7), 1.5 (3H,s, Me acetonide), 1.3 (3H, s, Me acetonide), 1.1 (3H, t, J=8Hz, $CH_3CH_2$).

EXAMPLE 5

Dihydroxylation with aqueous potassium permanganate.

A solution of potassium permanganate (2.39 g, 15.1 mmol) in water (100 ml) was added dropwise over 30 min to a stirred solution of the alkene [1(S),4(R)]-4-benzoylamino-N-ethylcyclopent-2-enecarboxamide (3.58 g, 13.9 mmol) in 1:3 water/acetone (100 ml) over 30 min. The reacton mixture was then filtered through Celite and the tiltrate treated with sodium metabisulphite until clear. The solvent was removed under reduced pressure and the residue taken up in 2,2-dimethoxypropane (150 ml) containg p-toluenesulphonic acid (50 mg). The resulting mixture was heated at reflux for 5 h, allowed to cool to room temperature, filtered through silica and the solvents removed under reduced pressure and the residue purified by chromatography (silica 2:1 to 3:1 ethyl acetate / pentane to give the acetonide (3d; 0.34 g), having the NMR spectrum as derailed in Example 4.

EXAMPLE 6

Dihydroxylation of [1(S),4(R)]-4-(t-butoxycarbonylamino)-methyl-2-cyclopentenecarboxylate.

A solution of [1(S),4(R)]-4-(t-butoxycarbonylamino)-methyl-2-cyclopentenecarboxylate (1.03 g, 4.27 mmol), osmium tetroxide (0.5 ml of a 0.5% wt aqueous solution) and 4-methylmorpholine-n-oxide (0.53 g, 4.5 mmol) in 5:1 acetone/water (30 ml) was heated at reflux for 5 h. 10% Sodium bisulfite (5 ml) and Florosil (5 g) were added and the solids filtered off. The solvents were removed under reduced pressure. The residue was taken up in 2:1 2,2- dimethoxypropane/acetone (30 ml) containing 4-toluenesulfonic acid (100 mg) and the solution heated at reflux for 4hrs. The solution was filtered through silica and concentrated under reduced pressure. The residue was purified by chromatography (silica, 4:1 pentane/ethyl acetate) to give the actonides (3g; 0.28 g) and (3h; 0.24 g). 3g:NMR (CDCl$_3$): δ4.9 (H, d, J=6hz, H-1), 4.4 (H, d, J=6hz, H-5), 4.0 (H, brm, H-6), 3.8 (3H, s, CH$_3$O), 3.4 (H, m, H-8), 2.2 (H, m, H-7), 1.4 (12H, s, Me acetonide and (CH$_3$)$_3$C), 1.2 (3H, s, Me acetonide).

3h:NMR (CDCl$_3$): δ5.0 (H, brd, NH), 4.8 (H, apparent t, H-1), 4.5 (H, apparent t, H-5), 3.8 (H, br m, H-6), 3.7 (3H, s, CH$_3$O), 2.6 (H, m, H-8), 2.0 (2h, m, 2H-7), 1.5 (12H, 2xs, CH$_3$C and(CH$_3$)$_3$C), 1.3 (3H, s, CH$_3$C).

EXAMPLE 7

Dihydroxylation of [1(R),4(R)]-4-(t-butoxycarbonylytamino)-methyl-2-cyclopentenecarboxylate.

A solution of [1(R),4(R)]-4-(t-butoxycarbonylylamino)-methyl-2-cyclopentenecarboxylate(1.14 g, 4.73 mmol), osmium teroxide (1 ml of a 0.5% wt aqueous solution), and 4-methylmorpholine-N-oxide (0.61 g, 5.21 mmol) in 4:1 acetone water (50 ml) was heated at reflux for 2 hrs. 5% Sodium bisulfite (10 ml) and Florosil (10 g) were added and the solids filtered off. The solvents were removed under reduced pressure. The residue was taken up in 4:1 2,2-dimethoxypropane/acetone (50 ml) containing 4-toluenesulfonic acid (20 mg) and the solution heated at reflux for 3 h. The mixture was filtered through silica and the solvent removed under reduced pressure. The residue was purified by chromatography (silica, 4:1 pentane/ethyl acetate) to give the acetonides (3i; 0.44 g) and (3j; 0.48 g).

3i: NMR (CDCl$_3$): δ5.0 (H, brd, NH), 4.8 (H, d, J=6Hz, H-1), 4.6 (H, apparent t, J=6Hz, H-5), 4.1 (H, m, H-6), 3.7 (3H, s, CH$_3$O), 2.8 (H, d, J=8Hz, H-8), 2.2 (H, m, H-7), 1.8 (H, m, H-7), 1.4 (12H, s,(CH$_3$)$_3$C and Me acetonide), 1.2 (3H, s, Me acetonide).

3j: NMR (CDCl$_3$): δ4.9 (H, t, J=6Hz, H-1), 4.7 (H, d, J=6Hz, H-5), 4.4 (H, brd, NH), 3.9 (H, t, J=6Hz, H-6), 3.7 (3H, s, CH$_3$O), 3.0 (H, m, H-8), 2.4 (H, brm, H-7), 1.7 H, brm, H-7), 1.4 (12H, s,( CH$_3$)$_3$C and Me acetonide), 1.3 (3H, s, Me acetonide).

EXAMPLE 8

Dihydroxylation of [1(R),4(R)]-4-(benzoylamino)-methyl-2-cyclopentenecarboxylate.

Osmium tetroxide (0.5ml of a 0.5% wt solution) was addd to a stirred solution of [1(R),4(R)]-4-(benzoylamino)-methyl-2-cyclopentenecarboxylate(0.74 g, 3.02 mmol) and 4-methylmorpholine-N-oxide (1 ml of a 60% wt aqueous solution) in acetone (25 ml) and the resulting solution heated at reflux for 2.5 h. A suspension of Florosil (10 g) in 10%sodium bisulphite (20 ml) was added and the resulting suspension filtered. The solvents were removed under reduced pressure. The residue was taken up in 2,2-dimethoxypropane (50 ml) containing 4-toluenesulfonic acid (50 mg) and the solution heated at reflux for 1.5 hrs. The solution was filtered through silica and concentrated under reduced pressure. The residue was purified by chromatography (silica, 2:1 pentane/ethyl acetate) to give the actonides (3k; 0.34 g) and (3l; 0.24 g).

3k: NMR (CDCl$_3$): δ7.9 (2H, m, ArH), 7.5 (3H, m, ArH), 6.6 (H, brd, NH), 4.9 (H, d, J=5.5Hz, H-1), 4.7 (H, apparent t, J=5.5Hz, H-5), 4.5 (H, m, H-6), 3.7 (3H, s, CH$_3$O), 3.0 (H, d, J=8Hz, H-8), 2.4 (H, m, H-7), 2.0 (H, m, H-7), 1.5 and 1.3 (2x3H, 2xs, 2x Me acetonide). 3l: NMR(CDCl$_3$): δ7.9 (2H, m, ArH), 7.4 (3H, m, ArH), 6.2 (H, brd, NH), 4.9 (H, apparent t, J=6Hz, H-1), 4.7 (H, d, J=5.5Hz, H-5), 4.3 (H, apparent t, J=6Hz, H-6), 3.7 (3H, s, CH$_3$O), 3.2 (H, m, H-8), 2.6 (H, m, H-7), 1.9 (H,m brdd, J=14, 7Hz, H-7), 1.4 and 1.2 (2x3H, 2xs, 2xMe acetonide).

Scheme 1

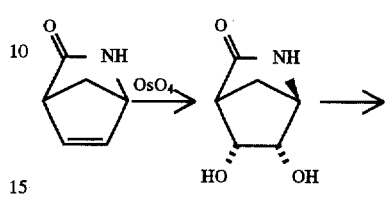

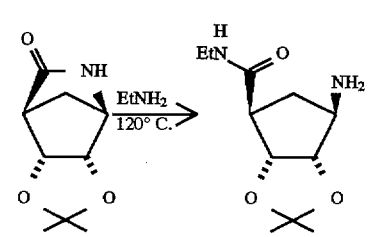

Scheme 2

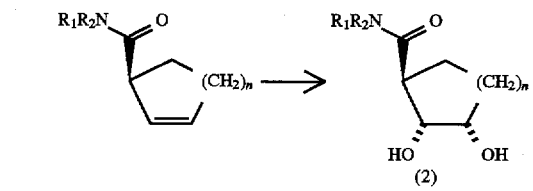

(2)

Scheme 3

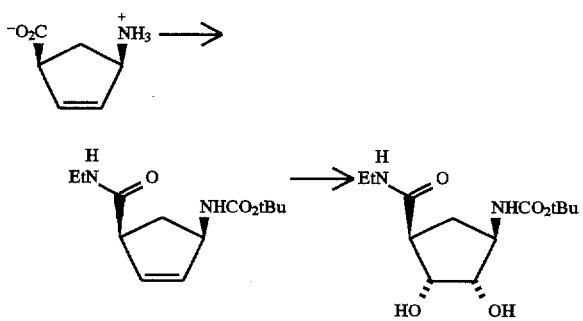

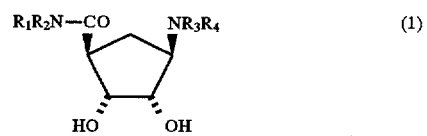

(1)

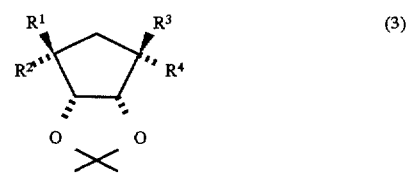

(3)

We claim:

1. A compound having the formula (1)

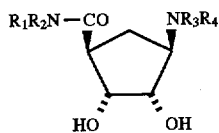

wherein $R_1$ is a hydrocarbyl group of up to 20 carbon atoms, $R_2$ is H or a hydrocarbyl group of up to 20 carbon atoms, and $R_3$ and $R_4$ are independently selected from H and removable blocking groups, or a salt thereof.

2. A compound according to claim 1, in the form of a substantially single diastereomer.

3. A compound according to claim 1, wherein $R_1$ is alkyl.

4. A compound according to claim 3, wherein $R_1$ is ethyl.

5. A compound according to claim 1, wherein $R_3$ is H and $R_4$ is H or a removable blocking group.

6. A compound according to claim 5, wherein said removable blocking group is a tert-butoxycarboxyl group or a benzyloxycarbonyl group.

7. A compound according to claim 1, wherein $R_2$ is H.

8. A process for preparing a 2,3-cis-dihydroxycycloalkane-1-carboxamide, which comprises dihydroxylation of the corresponding cycloalkene-1carboxamide.

9. A process according to claim 8, wherein the product is a 4-amine.

10. A process according to claim 8, wherein the dihydroxylation is conducted using $OsO_4$ or $KMnO_4$.

11. A process according to claim 8, which additionally comprises reaction of the product with an alkanediol, to give the corresponding acetonide.

12. A process according to claim 8, wherein said cycloalkene-1-carboxamide is a 2,3-cyclopentene-1-carboxamide.

13. A process according to claim 8, wherein said 2,3-cis-dihydroxycycloalkane-1-carboxamide has the formula (1)

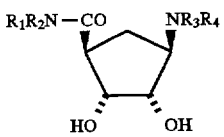

wherein $R_1$ is a hydrocarbyl group of up to 20 carbon atoms, R2 is H or a hydrocarbyl group of up to 20 carbon atoms, and $R_3$ and $R_4$ are independently selected from H and removable blocking groups, or a salt thereof.

14. A process according to claim 13, further comprising reacting the $NR_3R_4$ of said 2,3-cis-dihydroxycycloalkane-1-carboxamide to introduce a purine or a pyrimidine ring.

* * * * *